United States Patent
Liu et al.

(10) Patent No.: US 11,793,204 B2
(45) Date of Patent: Oct. 24, 2023

(54) BVP8 PROTEIN FOR KILLING TETRANYCHID MITES AND USE THEREOF

(71) Applicant: Hubei Biopesticide Engineering Research Center, Hubei (CN)

(72) Inventors: Xiaoyan Liu, Hubei (CN); Yong Min, Hubei (CN); Ling Chen, Hubei (CN); Lei Zhu, Hubei (CN); Yimin Qiu, Hubei (CN); Ben Rao, Hubei (CN); Ronghua Zhou, Hubei (CN); Yan Gong, Hubei (CN); Xianqing Liao, Hubei (CN); Wei Chen, Hubei (CN); Chunfu Qiu, Hubei (CN); Liqiao Shi, Hubei (CN); Jingzhong Yang, Hubei (CN)

(73) Assignee: Hubei Biopesticide Engineering Research Center, Hubei (CN)

( * ) Notice: Subject to any disclaimer, the term of this patent is extended or adjusted under 35 U.S.C. 154(b) by 0 days.

(21) Appl. No.: 17/832,566

(22) Filed: Jun. 3, 2022

(65) Prior Publication Data

US 2023/0011837 A1  Jan. 12, 2023

(30) Foreign Application Priority Data

Jul. 5, 2021 (CN) .......................... 202110755725.1

(51) Int. Cl.
*A01N 63/50* (2020.01)
*C07K 14/005* (2006.01)
*A01P 7/02* (2006.01)

(52) U.S. Cl.
CPC ................ *A01N 63/50* (2020.01); *A01P 7/02* (2021.08); *C07K 14/005* (2013.01); *C12N 2710/16722* (2013.01); *C12N 2710/16731* (2013.01)

(58) Field of Classification Search
CPC ........ A01N 63/50; A01N 37/46; A01N 63/60; A01P 7/02; C07K 14/005; C07K 14/00; C12N 2710/16722; C12N 2710/16731
See application file for complete search history.

(56) References Cited

PUBLICATIONS

Liu, Q., et al. Effect of the protein elicitor AMEP412 from Bacillus subtilis artificially fed to adults of the whitefly, Bemisia tabaci (Genn.) (Hemiptera: Aleyrodidae). Egypt J Biol Pest Control 30, 3 (2020). https://doi.org/10.1186/s41938-019-02 (Year: 2020).*

C.E.R. Dodd, Chapter 13—Infrequent Microbial Infections, Foodborne Diseases (Third Edition), Academic Press, 2017, pp. 277-288, ISBN 9780123850072. (https://www.sciencedirect.com/science/article/pii/B9780123850072000139) (Year: 2017).*

Khedher, S., et al., Bacillus amyloliquefaciens AG1 biosurfactant: Putative receptor diversity and histopathological effects on Tuta absoluta midgut. Journal of Invertebrate Pathology, vol. 132, 2015, pp. 42-47, https://doi.org/10.1016/j.jip.2015.08.010. (Year: 2015).*

Liu, X. and Huang D., Bacillus vallismortis NBIF-001 Genome, GenBank Registration No. CP020893.1 (Apr. 27, 2017).

* cited by examiner

*Primary Examiner* — Anna R Falkowitz
*Assistant Examiner* — Chantal Adlam
(74) *Attorney, Agent, or Firm* — MEI & MARK LLP; Manni Li

(57) ABSTRACT

A BVP8 protein for killing tetranychid mites and use thereof are provided. The protein is as set forth in SEQ ID NO. 2. The BVP8 protein has a median lethal concentration of 12.98 μg/mL against *Tetranychus urticae*, 33.45 μg/mL against *Panonychus citri*, and 26.32 μg/mL against *Tetranychus cinnabarinus*, and shows an inhibitory effect against the hatching and cleavage of *Tetranychus urticae* eggs, with the egg cleavage rate of 75.86% after 72 h. The protein provides a new option for the preparation of a novel miticide.

8 Claims, 1 Drawing Sheet
Specification includes a Sequence Listing.

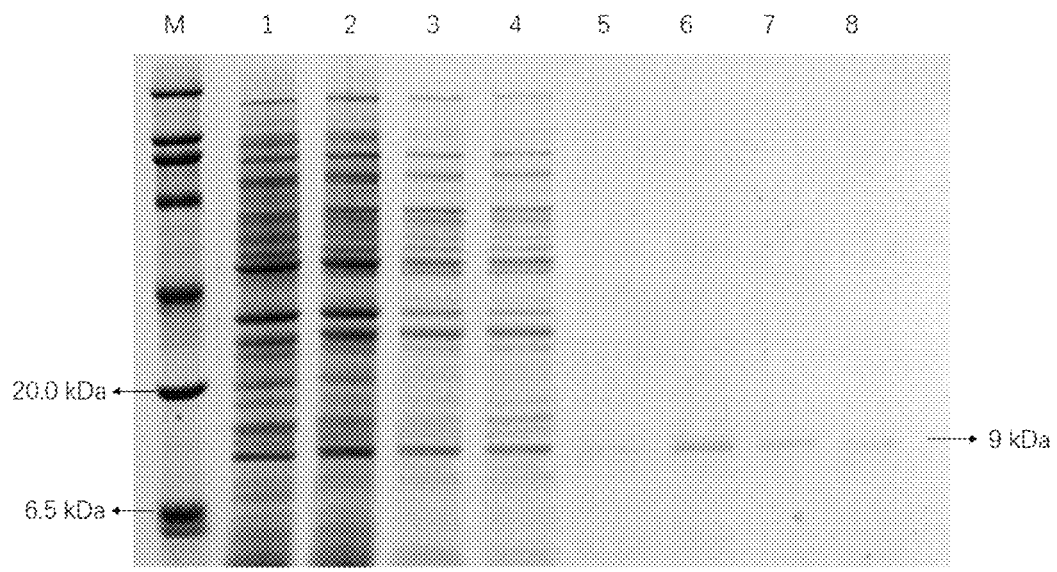
FIG. 1
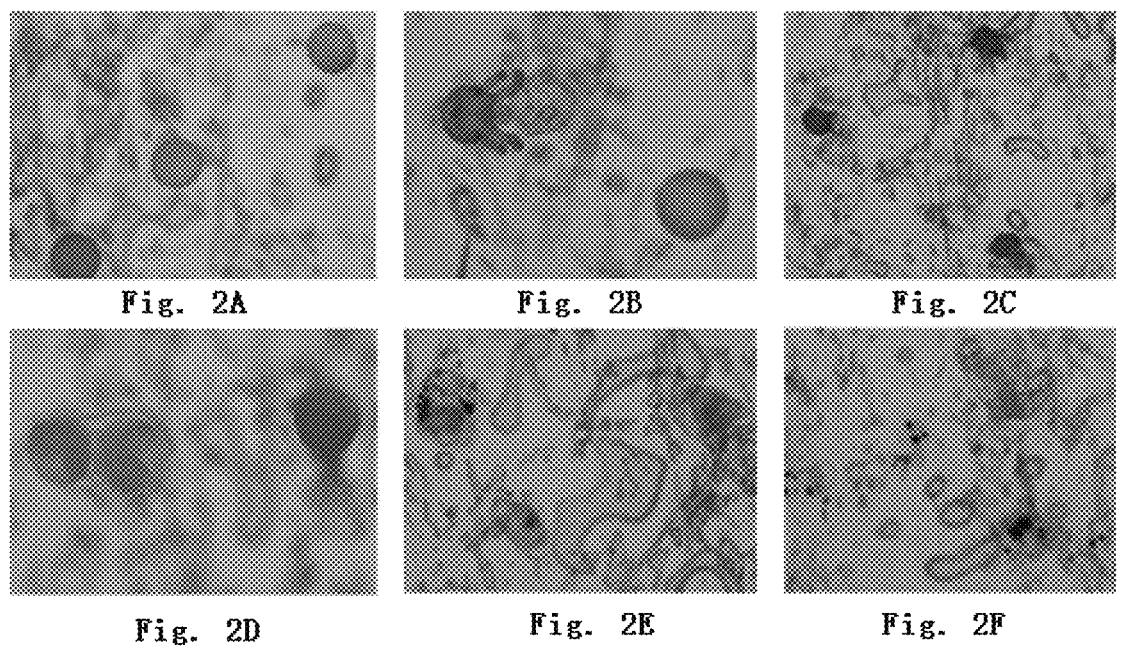
Fig. 2A  Fig. 2B  Fig. 2C
Fig. 2D  Fig. 2E  Fig. 2F

BVP8 PROTEIN FOR KILLING TETRANYCHID MITES AND USE THEREOF

CROSS-REFERENCE TO RELATED APPLICATIONS

The subject application claims priority on Chinese patent application no. 202110755725.1 filed on Jul. 5, 2021 in China. The contents and subject matters of the Chinese priority application is incorporated herein by reference.

BACKGROUND OF THE INVENTION

Technical Field

Tetranychid mites are serious pest mites in agricultural production and harmful to cotton, grain, fruit trees, forest trees, and ornamental plants. Cotton tetranychid mite (also called cotton spider mite) is one of the top ten pests in China. *Tetranychus urticae* can pierce 18-22 plant cells per minute. *Panonychus citri* is a serious pest mite to citrus trees, and *Panonychus ulmi* and *Tetranychus viennensis* are serious pest mites to fruit trees in northern China. In the case of serious damages, they can reduce the fruit yield by ⅓-⅔. *Petrobia latens* spreads all over the wheat-growing districts in China, and can lead to a total failure in wheat grains in the case of serious damages. There are many kinds of cotton tetranychid mites endangering cotton fields, which can reduce the yield by more than 30%, and even lead to totally withered cotton plants.

Temperature is an important factor affecting the population dynamics of tetranychid mites. The temperature range and suitable temperature for the activities of tetranychid mites vary with species. For *Panonychus ulmi* and other species that keep active at high temperature, their optimum growth temperature is 25-28° C.; and for *Bryobia* mites and other species that keep active at low temperature, their optimum growth temperature is 21-24° C. Most tetranychid mites prefer a dry climate, with an appropriate relative humidity of 40-70%. Therefore, a dry and hot weather often leads to rampant *Tetranychus* mites. The reproductive mode of *Tetranychus* mites mainly includes bisexual reproduction, and may also include *parthenogenesis*. For species such as *Bryobia rubrioculus*, only female mites are found, and they pertain to *Thelytokous parthenogensis*. For species such as *Tetranychus*, there are female and male mites, both sexual reproduction and *Thelytokous parthenogensis*, i.e., unfertilized female mites only producing male offspring, are available.

Methods for controlling the tetranychid mites mainly include agricultural control, biological control and chemical control. The agricultural control includes clearing orchards in winter and removing and intensively burning diseased leaves to reduce the number of pest mites living through the winter; and reinforcing the management of fertilizer and water to improve the microclimate of orchards, etc. The biological control includes controlling the mites by using green and safe means such as natural enemies and biologic miticides. The chemical control is mainly to control the mites by using chemicals such as chemical miticides. In recent years, due to the absence of substitute varieties to miticides, the miticides have been used heavily and repeatedly, which has accelerated the generation of resistance in pest mites and results in more and more serious mite damages, causing great economic losses to growers.

At present, most of the miticides developed across the world are chemical substances or macromolecular antibiotics, which are insoluble in water, and micromolecular proteinaceous substances have been less reported. Based on the above background, it is necessary to develop a proteinaceous agent for controlling the tetranychid mites for use in the field of biological control of the tetranychid mites, which is of important production and practice significance.

BRIEF SUMMARY OF THE INVENTION

An object of the invention is to provide a protein, as set forth in SEQ ID NO:2, for killing tetranychid mites.

Another object of the invention is to provide use of the protein for killing tetranychid mites in the preparation of a biocide against tetranychid mites.

To achieve the above objects, a technical measure used in the invention is as follows.

A protein for killing tetranychid mites is as set forth in SEQ ID NO:2; and a gene encoding the protein as set forth in SEQ ID NO:2 also falls within the protection scope of the invention. Preferably, the gene is as set forth in SEQ ID NO:1.

The protein prepared by a conventional means, such as prokaryotic expression, eukaryotic expression, or direct synthesis, in the art also falls within the protection scope of the invention.

The use of the protein for killing tetranychid mites in the preparation of a biocide against tetranychid mites includes the preparation of the biocide against tetranychid mites by taking the protein as set forth in SEQ ID NO:2 as an effective ingredient, or as a sole effective ingredient. The protein for killing tetranychid mites according to the invention is also applicable to a hatching inhibitor against tetranychid mite eggs.

During the above use, preferably, the tetranychid mites are *Tetranychus urticae*, *Panonychus citri*, or *Tetranychus cinnabarinus*.

Compared with the prior art, the invention has the following characteristics.

The invention reports a novel protein for killing tetranychid mites and a miticidal activity thereof for the first time, which provides a new option for the preparation of a novel miticide.

The miticide containing the BVP8 protein has the advantages of high efficiency, low toxicity, and environmental friendliness.

BRIEF DESCRIPTION OF THE SEVERAL VIEWS OF THE DRAWINGS

FIG. 1 shows the sodium dodecyl sulfate-polyacrylamide gel electrophoresis (SDS-PAGE) analysis of the purified BVP8 protein of the present invention.

FIGS. 2A to 2F show the effects of the BVP8 protein of the present invention against *Tetranychus urticae* mite eggs, where FIG. 2A to 2C show the effects of control group after 24 hours, 48 hours, and 72 hours, respectively, after administration; and FIGS. 2D to 2F show the effects of the BVP8 protein of the present invention after 24 hours, 48 hours, and 72 hours, respectively after administration.

DETAILED DESCRIPTION OF THE INVENTION

Experimental methods in the embodiments below are all conventional microbiological operation methods that have been reported, unless otherwise specified. Reagents or materials as mentioned are those used in conventional solutions in the art, unless otherwise specified.

The BVP8 protein mentioned in the invention can be prepared by a conventional method, such as prokaryotic expression and commercial synthesis, in the art. The present invention illustrates the mite inhibition function of a prokaryotically expressed BVP protein, by way of example. This protein derived by other means may also exert the same effect.

Embodiment 1

Preparation of Miticidal Protein BVP8

(1) Based on a sequence (encoding a protein as set forth in SEQ ID NO. 2) as set forth in SEQ ID NO.1, a BVP8 protein gene fragment (from Sangon Biotech (Shanghai) Co., Ltd.) was artificially synthesized, and then attached to a pET 28a plasmid of *Escherichia coli* expression vector to construct a recombinant expression plasmid pET28a-BVP8.

(2) Expression and Purification of Miticidal BVP 8 Protein Gene in *Escherichia coli* BL21

To express the miticidal BVP8 protein at a high level, the above-mentioned recombinant expression plasmid pET28a-BVP8 carrying a coded sequence was transformed into *Escherichia coli* BL21 to prepare recombinant bacteria BL21/pET28a-BVP8. The recombinant bacteria were inoculated into 5 mL of Luria-Bertani (LB) liquid medium, and cultured in a shaker at 37° C. until OD600 was 0.6. Then, 1.0 mmol/L isopropyl-B-D-thiogalactoside (IPTG, from Sigma) was added for induced culturing for 3 h at 30° C. 50 mL of a 3-hour induced culture of the above-mentioned recombinant bacteria BL21/pET28a-BVP8 was centrifuged at 12,000 rpm for 30 s to collect bacterial cells. Bacteria cells were disrupted by ultrasonic waves (technical parameters: 300 W; 30 s; and 30 s interval), and then centrifuged at 12,000 for 15 min to obtain a supernatant, which was filtered with a filter membrane having a pore size of 0.45 μm to remove impurities. Proteins were purified by the affinity chromatography for His fusion proteins. A final purified product was detected by SDS-PAGE, with the results shown in FIG. 1. The purified proteins were aligned with a protein molecular weight marker to derive an estimated molecular weight of 9 kDa, which was basically in line with the molecular weight of 8.34 kDa as predicted for the BVP8 protein. This demonstrated the successful expression of the BVP8 protein of the invention in *Escherichia coli* B21.

Embodiment 2

(1) BVP8 Protein for Killing *Tetranychus urticae*:

Referring to the standard method for determining pest mites, namely, the slide dipping method, recommended by Food and Agriculture Organization of the United Nations (FAO), a double-faced adhesive tape was cut into pieces of 2-3 cm long and stuck to one end of a microscope slide, and paper on the adhesive tape was removed with tweezers. Female adult mites with similar size, bright body color and high vitality were picked with a Chinese writing brush #0, and were stuck to the double-faced adhesive tape at backs (note: the feet, whiskers and mouthparts of the mites should not be stuck), with 4 lines stuck to each piece and 10 mites in each line. The mites were placed and left in a biochemical incubator with the temperature of 25 and the relative humidity of approx. 85% for 4 h, and then were observed with binoculars. Dead or inactive individuals were eliminated. An agent was diluted by 5-7 times with water based on a preliminary test. The end of the slide with the mites was dipped into the agent solution, shook gently for 5 s and then taken out. The mites as well as the excessive agent solution therearound were rapidly dried with absorbent paper. The slide was placed and left in the above-mentioned biochemical incubator. After 24 h, the results were checked with the binoculars. The bodies of the mites were lightly touched with the Chinese brush pen, and those without any motion of feet were considered to be dead. The test was repeated three times at each concentration, and the mites dipped in fresh water were additionally taken as a control. Following the experimental steps above, the bioassay result of a BVP8 protein suspension against *Tetranychus urticae* was shown in Table 1 below, which was 12.98 μg/mL. An $LC_{50}$ value was calculated by using SPASS 19.0 data processing software.

TABLE 1

Miticidal activity of BVP8 protein against *Tetranychus urticae*

| Dose (μg/mL) | Mortality (%) | Logarithmic dose | Probability unit (P + 5) | Regression equation | Medial lethal concentration ($LC_{50}$, μg/mL) |
|---|---|---|---|---|---|
| 165.5 | 56.7 | 2.219 | 5.170 | Y = 4.7430 + 0.2308X (r = 0.5130) | 12.98 |
| 82.75 | 58.3 | 1.918 | 5.210 | | |
| 33.1 | 62.5 | 1.520 | 5.320 | | |
| 16.55 | 44.4 | 1.219 | 4.859 | | |

(2) BVP8 Protein for Killing *Panonychus citri*:

Referring to the standard method for determining pest mites, namely, the slide dipping method, recommended by Food and Agriculture Organization of the United Nations (FAO), a double-faced adhesive tape was cut into pieces of 2-3 cm long and stuck to one end of a microscope slide, and paper on the adhesive tape was removed with tweezers. Female adult mites with similar size, bright body color and high vitality were picked with a Chinese writing brush #0, and were stuck to the double-faced adhesive tape at backs (note: the feet, whiskers and mouthparts of the mites should not be stuck), with 4 lines stuck to each piece and 10 mites in each line. The mites were placed and left in a biochemical incubator with the temperature of 25 and the relative humidity of approx. 85% for 4 h, and then were observed with binoculars. Dead or inactive individuals were eliminated. An agent was diluted by 5-7 times with water based on a preliminary test. The end of the slide with the mites was dipped into the agent solution, shook gently for 5 s and then taken out. The mites as well as the excessive agent solution therearound were rapidly dried with absorbent paper. The slide was placed and left in the above-mentioned biochemical incubator. After 24 h, the results were checked with the binoculars. The bodies of the mites were lightly touched with the Chinese brush pen, and those without any motion of feet were considered to be dead. The test was repeated three times at each concentration, and the mites dipped in fresh water were additionally taken as a control. Following the experimental steps above, the bioassay result of a BVP8 protein suspension against *Panonychus citri* was shown in Table 2 below, which was 33.45 µg/mL. An $LC_{50}$ value was calculated by using SPASS 19.0 data processing software.

TABLE 2

Miticidal activity of BVP8 protein against *Panonychus citri*

| Dose (µg/mL) | Mortality (%) | Logarithmic dose | Probability unit (P + 5) | Regression equation | Medial lethal concentration ($LC_{50}$, µg/mL) |
|---|---|---|---|---|---|
| 165.5 | 76.9 | 2.591 | 2.219 | Y = 3.5091 + 0.9780X (r = 0.9781) | 33.45 |
| 82.75 | 63.6 | 1.892 | 1.918 | | |
| 33.1 | 45.5 | 1.591 | 1.520 | | |
| 16.55 | 41.7 | 1.289 | 1.219 | | |

(3) Following the experimental steps above, the bioassay result of a BVP8 protein suspension against *Tetranychus cinnabarinus* was shown in Table 3 below, which was 26.32 µg/mL. An $LC_{50}$ value was calculated by using SPASS 19.0 data processing software.

TABLE 3

Miticidal activity of BVP8 protein against *Tetranychus cinnabarinus*

| Dose (µg/mL) | Mortality (%) | Logarithmic dose | Probability unit (P + 5) | Regression equation | Medial lethal concentration ($LC_{50}$, µg/mL) |
|---|---|---|---|---|---|
| 165.5 | 97.2 | 2.219 | 6.918 | Y = 1.8201 + 2.2390X (r = 0.9904) | 26.32 |
| 82.75 | 82.1 | 1.918 | 5.922 | | |
| 33.1 | 59.5 | 1.520 | 5.239 | | |
| 16.55 | 34.3 | 1.219 | 4.596 | | |

(4) Inhibitory Effect of BVP8 Protein Against *Tetranychus urticae* Eggs

Leaf blades with *Tetranychus urticae* eggs at a full egg period were collected and flushed under running water to remove adult and nymph mites. Absorbent paper was used to absorb water on the leaf blades. The eggs were gently taken down by using a slide with double-faced tape stuck thereto, and observed and counted under a microscope. After counting, the eggs were dipped into a sample to be detected for 3 seconds and then taken out. Then, the eggs were placed into a constant-temperature incubator at 25° C., and observed under the microscope after 24 hr, 48 hr and 72 hr respectively in terms of the inhibitory effect of the BVP8 protein against the *Tetranychus urticae* eggs. The eggs having different forms were counted and photographed.

Results show that the BVP8 protein has an inhibitory effect on the *Tetranychus urticae* eggs, is capable of inhibiting the hatching of eggs, which start atrophy and are gradually cleaved after 24 hr, with the cleavage rates at 48 hr and 72 hr being 22.41% and 75.86% respectively (Table 4, FIGS. 2A to 2F).

TABLE 4

Inhibitory effect of BVP8 protein against *Tetranychus urticae* eggs

| | 0 hr | | 24 hr | | 48 hr | | 72 hr | |
|---|---|---|---|---|---|---|---|---|
| Designation | State | Hatching rate (%) | State | Hatching rate (%) | State | Hatching rate (%) | State | Hatching rate (%) |
| BVP8 protein | + | 0 | ++++ | 0 | ++++ | 0 | +++++ | 0 |
| Fresh water as control | + | 0 | ++ | 17.86 | +++ | 50 | +++ | 83.93 |

Note:
+: pale-yellow full eggs to be hatched; ++: normal eggs that have been hatched partially; +++: hatched eggs; ++++: unhatched shrunk eggs; +++++: cleaved eggs.

What is claimed is:

1. A method for controlling tetranychid mites, comprising spraying a biocide comprising a protein of SEQ ID NO:2 on tetranychid mites.

2. The method according to claim 1, wherein the tetranychid mites are *Tetranychus urticae, Panonychus citri,* or *Tetranychus cinnabarinus*.

3. The method according to claim 1, wherein the protein of SEQ ID NO:2 has a median lethal concentration of 12.98 μg/mL against *Tetranychus urticae*.

4. The method according to claim 1, wherein the protein of SEQ ID NO:2 has a median lethal concentration of 33.45 μg/mL against *Panonychus citri*.

5. The method according to claim 1, wherein the protein of SEQ ID NO:2 has a median lethal concentration of 26.32 μg/mL against *Tetranychus cinnabarinus*.

6. A method for inhibiting hatching of tetranychid mite eggs, comprising
spraying a biocide containing a protein as set forth in SEQ ID NO:2 to eggs of tetranychid mites.

7. The method according to claim 6, wherein the tetranychid mites are *Tetranychus urticae, Panonychus citri,* or *Tetranychus cinnabarinus*.

8. The method according to claim 6, wherein a cleavage rate is 75.86% or less at 72 hours after spraying the biocide for *Tetranychus urticae* eggs.

* * * * *

SEQUENCE LISTING

<160> NUMBER OF SEQ ID NOS: 2

<210> SEQ ID NO 1
<211> LENGTH: 231
<212> TYPE: DNA
<213> ORGANISM: Bacillus vallismortis

<400> SEQUENCE: 1
ttgttcggac caattttaaa agcattaaaa gctcttgtat ctaaagtacc gtggggtaag      60
gtcgcatcat tcttaaaatg ggcaggtaac ttagctgctg cagccgctaa atattcatat     120
acaagtggaa agaaaatcct tgcgtatatc caaaaacacc caggaaaaat cgttgattgg     180
ttcctaaaag gatattctgt atacgacgtt attaaaatga ttcttggcta a              231

<210> SEQ ID NO 2
<211> LENGTH: 70
<212> TYPE: PRT
<213> ORGANISM: Bacillus vallismortis

<400> SEQUENCE: 2

Met Phe Gly Pro Ile Leu Lys Ala Leu Lys Ala Leu Val Ser Lys Val
1               5                   10                  15

Pro Trp Gly Lys Val Ala Ser Phe Leu Lys Trp Ala Gly Asn Leu Ala
            20                  25                  30

Ala Ala Ala Lys Tyr Ser Tyr Thr Ser Gly Lys Lys Ile Leu Ala
        35                  40                  45

Tyr Ile Gln Lys His Pro Gly Lys Ile Val Asp Trp Phe Leu Lys Gly
    50                  55                      60

Tyr Ser Val Tyr Asp Val
65                  70